United States Patent [19]

Brady et al.

[11] 4,098,821

[45] Jul. 4, 1978

[54] QUATERNARY AMMONIUM PHENATES CONTAINING A (3-CHLORO-2-PROPENYL) GROUP

[75] Inventors: Thomas P. Brady, Holliston; Nancy L. Boardway, Ashland, both of Mass.; Joseph W. Whalen, Midland, Mich.

[73] Assignee: The Dow Chemical Company, Midland, Mich.

[21] Appl. No.: 733,607

[22] Filed: Oct. 18, 1976

[51] Int. Cl.$^2$ .................. C07C 87/26; A01N 9/20
[52] U.S. Cl. .................. 260/567.5; 424/329
[58] Field of Search .................. 260/567.6 M, 567.5; 424/329

[56] References Cited

U.S. PATENT DOCUMENTS

| | | | |
|---|---|---|---|
| 2,817,664 | 12/1959 | Cavillito et al. | 260/567.6 M |
| 3,510,248 | 5/1970 | Thielen et al. | 260/567.6 M |
| 3,700,399 | 10/1972 | Shimauchi et al. | 260/567.6 M |
| 3,714,256 | 1/1973 | Samour | 260/567.6 M |
| 3,959,376 | 5/1976 | Trapasso | 260/567.6 M |
| 3,960,958 | 6/1976 | Richardson | 260/567.5 |
| 3,987,097 | 10/1976 | Matter et al. | 262/567.6 M |
| 4,025,556 | 5/1977 | Schillenbaum et al. | 260/567.6 M |

Primary Examiner—James O. Thomas, Jr.
Assistant Examiner—James H. Reamer
Attorney, Agent, or Firm—Theodore Post; C. Kenneth Bjork; Daniel L. DeJoseph

[57] ABSTRACT

Quaternary ammonium phenates containing a 3-chloro-2-propenyl substituent group attached to the nitrogen atom and having as other substitutent groups attached to the nitrogen atoms (1) a $C_8$–$C_{18}$ alkyl group, (2) a one carbon, two carbon, $C_8$–$C_{18}$ alkyl or a 3-chloro-2-propenyl group, (3) a one carbon or two carbon alkyl or a 3-chloro-2-propenyl group, and (4) a phenate group, wherein not more than a total of two 3-chloro-2-propenyl groups are present in the molecule. The compounds have antibacterial and antifungal utility.

5 Claims, No Drawings

QUATERNARY AMMONIUM PHENATES CONTAINING A (3-CHLORO-2-PROPENYL) GROUP

SUMMARY OF THE INVENTION

A novel quaternary ammonium phenate is prepared by reacting (A) a quaternary ammonium chloride having a 3-chloro-2-propenyl substituent group attached to the nitrogen and having as other substituent groups (1) a $C_8$-$C_{18}$ alkyl group; (2) a 3-chloro-2-propenyl substituent group or a methyl, ethyl, or $C_8$ to $C_{18}$ alkyl substituent group attached to the nitrogen; (3) a one or two carbon alkyl or a 3-chloro-2-propenyl group attached to the nitrogen, and wherein a total of not more than two 3-chloro-2-propenyl groups are attached to the nitrogen atom with (B) a substantially equimolar proportion of an alkali metal phenate, the benzene nucleus of which may be substituted with 1 to 5 halo groups, or a phenyl, phenoxy, $C_1$ to $C_4$ alkyl, a $C_1$ to $C_4$ alkoxy or an amino group. Other salt forms than the quaternary ammonium chloride salt can be used in the reaction, for example, any inorganic salt such as the bromide, the iodide, the sulfate, the nitrate or the phosphate. The reaction medium is a $C_1$ to $C_4$ alkanol, advantageously ethanol.

The reaction is illustrated by the following schematic equation:

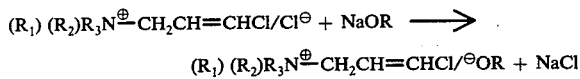

$$(R_1)(R_2)R_3 N^{\oplus}-CH_2CH=CHCl/Cl^{\ominus} + NaOR \longrightarrow$$
$$(R_1)(R_2)R_3 N^{\oplus}-CH_2CH=CHCl/^{\ominus}OR + NaCl$$

In the equation, $R_1$ represents a $C_8$ to $C_{18}$ alkyl group, $R_2$ represents methyl, ethyl, a $C_8$ to $C_{18}$ alkyl group or a 3-chloro-2-propenyl group, $R_3$ represents methyl, ethyl or a 3-chloro-2-propenyl group, and R represents phenyl or substituted phenyl wherein the substituents are 1 to 5 halo groups, or a phenyl, phenoxy, $C_1$ to $C_4$ alkyl or alkoxy group, or an amino group, and wherein only one of $R_2$ and $R_3$ can be 3-chloro-2-propenyl.

Thus, the quaternary ammonium salts may be N-(3-chloroallyl)-N,N-dimethyl-N-dodecylammonium chloride, bromide, sulfate, nitrate or phosphate; N-(3-chloro-2-propenyl)-N,N-dimethyl-N-decylammonium chloride and other inorganic salts; N,N-bis(3-chloro-2-propenyl)-N-methyl-N-octadecylammonium chloride and similar inorganic salts. The alkali metal phenates which are useful in the preparation of the compounds of this invention include, for example, the alkali metal, and, advantageously, the sodium salts of the following: pentachlorophenol; 2,4,5-trichlorophenol; o-phenylphenol; 2,4-dichlorophenol; 4-phenoxyphenol; 3-methoxyphenol; and 3-aminophenol.

DESCRIPTION OF SOME PREFERRED EMBODIMENTS

In accordance with the present invention, the quaternary ammonium phenates herein claimed are readily prepared in high yield in a one-step process from the corresponding quaternary ammonium salt by mixing together an ethanolic solution of the latter with a solution of an alkali metal phenate salt in the same solvent. A precipitate of by-product salt forms. The product is obtained by evaporation of the solvent. The proportions of reactants are substantially equimolar with reference to the quaternary ammonium salt and the phenate salt. The reaction solvent may be used in large excess, but the preferred concentration of reactants is less than about 50% and greater than about 30%. The reaction temperature is advantageously maintained at substantially reflux temperature. As noted earlier, the quaternary ammonium salt reactant may be any mineral acid salt, advantageously the chloride. The phenate salt may be any alkali metal or ammonium salt, advantageously the sodium salt. In place of ethanol, methanol may be used. The products are amber-colored oils, soluble in water and in polar organic solvents.

The following additional description and examples further describe the invention and the manner and process of making and using it to enable the art skilled to make and use the same and set forth the best mode contemplated by the inventors of carrying out the invention.

EXAMPLE 1

Preparation of N-(3-chloro-2-propenyl)-N,N-dimethyl-N-dodecylammonium 2,4-dichlorophenate A solution of 7.40 g (0.040 mole) sodium 2,4-dichlorophenate in 50 ml absolute ethanol was added at room temperature to a stirred solution of 12.98 g (0.040 mole) N-(3-chloro-2-propenyl)-N,N-dimethyl-dodecylammonium chloride in 60 ml absolute ethanol. A precipitate of sodium chloride started to form immediately. After stirring for two hours, the reaction mixture was filtered and the filtrate concentrated to remove solvent. The residue, an amber oil, weighed 17.5 g (90% yield). NMR and elemental analysis indicated that the monohydrate of the desired product had been isolated.

| Analysis: | | | | |
|---|---|---|---|---|
| C% | Th. | 59.97, | Fd. | 60.03 |
| H% | Th. | 8.55, | Fd. | 8.75 |
| N% | Th. | 2.99, | Fd. | 3.15 |
| Cl% | Th. | 22.65, | Fd. | 22.74 |

In a similar manner, the following compounds were prepared:

$R_1(R_2)(R_3)N^{\oplus}-CH_2CH=CHCl/X^{\ominus}$

| Cpd. No. | $R_1$ | $R_2$ | $R_3$ | X (phenate) |
|---|---|---|---|---|
| 1. | n-$C_{12}H_{25}$ | $CH_3$ | $CH_3$ | 2,4,6-$Cl_3$ |
| 2. | n-$C_{12}H_{25}$ | $CH_3$ | $CH_3$ | 2,4,5-$Cl_3$ |
| 3. | n-$C_{12}H_{25}$ | $CH_3$ | $CH_3$ | o-phenyl |
| 4. | n-$C_{12}H_{25}$ | $CH_3$ | $CH_3$ | 4-bromo |
| 5. | n-$C_{12}H_{25}$ | $CH_3$ | $CH_3$ | 2,3,5,6-$Cl_4$ |
| 6. | n-$C_{12}H_{25}$ | $CH_3$ | $CH_3$ | 3-amino |
| 7. | n-$C_{12}H_{25}$ | $CH_3$ | $CH_3$ | 3-methyl |
| 8. | n-$C_{12}H_{25}$ | $CH_3$ | $CH_3$ | 3,4-dimethyl |
| 9. | n-$C_{12}H_{25}$ | $CH_3$ | $CH_3$ | 4-Cl-2-cyclopentyl |
| 10. | n-$C_{12}H_{25}$ | $CH_3$ | $CH_3$ | 2-chloro-4-phenyl |
| 11. | n-$C_{12}H_{25}$ | $CH_3$ | $CH_3$ | 4-[1-(4-hydroxyphenyl)-1-methylethyl] |
| 12. | n-$C_{12}H_{25}$ | $C_2H_5$ | $C_2H_5$ | $Cl_5$ |
| 13. | n-$C_{18}H_{37}$ | $CH_3$ | $CH_3$ | $Cl_5$ |
| 14. | n-$C_{18}H_{37}$ | $CH_3$ | $CH_2CH=CHCl$ | $Cl_5$ |
| 15. | n-$C_{12}H_{25}$ | $CH_3$ | $CH_3$ | 2,4,6-$Br_3$ |
| 16. | n-$C_{12}H_{25}$ | $CH_3$ | $CH_3$ | $Cl_5$ |

All of the compounds of this invention have antimicrobial utility. In conventional in vitro agar Petri dish dilution tests for determining bactericidal and fungicidal activity, the following representative compounds had the indicated minimum inhibitory concentrations (MIC) in parts per million:

| Compound | MIC, ppm | | | | | | |
|---|---|---|---|---|---|---|---|
| | S.a. | S.t. | E.a. | C.p. | A.n. | T.m. | C.a. |
| 1 | 100 | 500 | >500 | 500 | 100 | 100 | 500 |
| 2 | 25 | 50 | 100 | 25 | 25 | 10 | 25 |
| 3 | 10 | 250 | 250 | 250 | 250 | 75 | 250 |
| 4 | 10 | 500 | >500 | 500 | 500 | 100 | 500 |
| 5 | 100 | 500 | >500 | 100 | 100 | 100 | 100 |
| 6 | 100 | >500 | >500 | 100 | 100 | 100 | 100 |
| 7 | 10 | >500 | >500 | 100 | 500 | 100 | 100 |
| 8 | 10 | 500 | >500 | 100 | 100 | 100 | 100 |
| 9 | 100 | 500 | >500 | 500 | >500 | 500 | 500 |
| 10 | 100 | 500 | >500 | 500 | 100 | 100 | 500 |
| 11 | 100 | >500 | >500 | >500 | >500 | 500 | >500 |
| 16 | 10 | 250 | 500 | 10 | 25 | 25 | 25 |

S.a. = *S. aureus*, S.t. = *typhosa*, E. a. = *E. aerogenes*, C.p. = *C. pelliculosa*, A.n. = *A. niger*, T.m. = *A. T. mentagrophytes*, C.a. = *C. alibicans*

While all the compounds of this invention are useful as antimicrobial agents, there are, as shown, variations with respect to their bactericidal and fungicidal activity against the same microbes or at the same concentration.

The quaternary ammonium halide starting materials are made by reacting 1,3-dichloropropene with a corresponding tertiary amine precursor in an organic solvent, then recovering the product. Representative of such preparations, a solution of 4.0 g (0.036 mole) 1,3-dichloropropene in 25 ml ether was added all at once to a solution of 21.3 g (0.10 mole) N,N-dimethylhexadecylamine in 25 ml ether. The reaction mixture was heated at reflux for about 2 hours to substantial completion of reaction, i.e., to completion of formation of the quaternary ammonium chloride. Evaporation of the solvent gave a viscous oil which, after recrystallization from acetone, gave 12.5 g (90% yield) of white crystals, melting at 54°–56° C. NMR and elemental analysis indicated the monohydrate of product N-(3-chloro-2-propenyl)-N,N-dimethylhexadecylammonium chloride had been isolated.

What is claimed is:

1. A compound represented by the formula

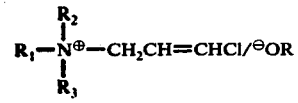

wherein $R_1$ is a $C_8$–$C_{18}$ alkyl group, $R_2$ is methyl, ethyl, a $C_8$–$C_{18}$ alkyl or a 3chloro-2-propenyl group, $R_3$ is methyl, ethyl or a 3-chloro-2-propenyl group and R is phenyl or phenyl substituted with 1 to 5 halo groups, phenyl, phenoxy, $C_1$–$C_4$ alkyl or alkoxy, or amino, wherein only one of $R_2$ and $R_3$ can be 3-chloro-2-propenyl.

2. The compound of claim 1 which is N-(3-chloro-2-propenyl)-N,N-dimethyl-N-dodecylammonium 2,4-dichlorophenate.

3. The compound of claim 1 which is N-(3-chloro-2-propenyl)-N,N-dimethyl-N-dodecylammonium pentachlorophenate.

4. The compound of claim 1 which is N-(3-chloro-2-propenyl)-N,N-dimethyl-N-dodecylammonium 2,4,5-trichlorophenate.

5. The compound of claim 1 which is N-(3-chloro-2-propenyl)-N,N-dimethyl-N-dodecylammonium o-phenylphenate.

* * * * *

UNITED STATES PATENT AND TRADEMARK OFFICE
CERTIFICATE OF CORRECTION

PATENT NO. : 4,098,821

DATED : July 4, 1978

INVENTOR(S) : Thomas P. Brady, et al.

It is certified that error appears in the above-identified patent and that said Letters Patent are hereby corrected as shown below:

Column 3, line 14, "S.t. = typhosa" should read -- S.t. = S. typhosa --;

Column 3, line 15, "A.T. mentagrophytes, C.a. = C. alibicans" should read -- T. mentagrophytes, C.a. = C. albicans --;

Column 4, line 14, "3chloro" should read -- 3-chloro --.

Signed and Sealed this

Fifth Day of June 1979

[SEAL]

Attest:

RUTH C. MASON
Attesting Officer

DONALD W. BANNER
Commissioner of Patents and Trademarks